(12) United States Patent
Corbeil et al.

(10) Patent No.: US 7,809,422 B2
(45) Date of Patent: Oct. 5, 2010

(54) METHOD AND APPARATUS FOR OPTICAL IMAGING

(75) Inventors: Luc Corbeil, Ste-Anne-des-Lacs (CA); Peter Marin, Kanata (CA); Mario Gagnon, Montreal (CA); Benoît Orban, St-Lambert (CA); Christian Pilon, Montreal (CA)

(73) Assignee: ART Advanced Research Technologies Inc., Montreal, Quebec (CA)

( * ) Notice: Subject to any disclaimer, the term of this patent is extended or adjusted under 35 U.S.C. 154(b) by 496 days.

(21) Appl. No.: 10/290,485

(22) Filed: Nov. 8, 2002

(65) Prior Publication Data

US 2004/0092826 A1 May 13, 2004

(51) Int. Cl.
*A61B 5/00* (2006.01)

(52) U.S. Cl. ............... 600/407; 600/417; 600/425; 600/427; 600/437; 600/449; 600/459; 600/461; 378/37

(58) Field of Classification Search ........... 600/421, 600/476, 407, 424, 425, 427, 473, 417, 437, 600/449, 459, 461; 606/2, 13; 607/91
See application file for complete search history.

(56) References Cited

U.S. PATENT DOCUMENTS

| | | | |
|---|---|---|---|
| 3,165,630 A | | 1/1965 | Bielat et al. |
| 3,973,126 A | | 8/1976 | Redington et al. |
| 4,015,836 A | * | 4/1977 | Redington et al. ............ 5/601 |
| 4,186,747 A | * | 2/1980 | Iinuma ........................ 600/444 |
| 4,341,222 A | | 7/1982 | Gardineer et al. |
| 4,731,060 A | * | 3/1988 | Catalano ..................... 604/254 |
| 5,059,173 A | * | 10/1991 | Sacco .......................... 604/80 |
| 5,289,520 A | | 2/1994 | Pellegrino et al. |
| 5,409,497 A | | 4/1995 | Siczek et al. |
| 5,415,169 A | | 5/1995 | Siczek et al. |
| 5,564,438 A | | 10/1996 | Merchant |
| 5,569,266 A | | 10/1996 | Siczek |

(Continued)

FOREIGN PATENT DOCUMENTS

DE    10026792    6/2001

(Continued)

OTHER PUBLICATIONS

"Pear-shaped" WordNet® 2.0. 2003. Princeton University, cited at http:// dictionary.reference.com/search?q=Pear-shaped&r=66, last accessed Dec. 12, 2005.*

*Primary Examiner*—Brian Casler
*Assistant Examiner*—Baisakhi Roy
(74) *Attorney, Agent, or Firm*—BCF LLP (57) ABSTRACT

An apparatus for optical imaging of a breast is described, the apparatus comprising: a supporting platform for positioning a patient in a face down prone position, the platform having a cavity for the breast to be pendantly suspended therethrough; a flexible fluid-filled receptacle below the cavity holding an optical matching fluid for the optical imaging, wherein the breast is immersed in the fluid during the optical imaging; a supporting mechanism surrounding a perimeter of the receptacle for supporting the receptacle within the cavity and preventing it from falling through the cavity when holding the optical matching fluid; and a source and detector coupling device for orienting source and detector ports with respect to the receptacle and for contacting the receptacle to obtain a desired geometry of the breast and the optical matching fluid.

15 Claims, 7 Drawing Sheets

U.S. PATENT DOCUMENTS

| | | | |
|---|---|---|---|
| 5,599,303 A * | 2/1997 | Melker et al. | 604/80 |
| 5,609,152 A | 3/1997 | Pellegrino et al. | |
| 5,855,554 A | 1/1999 | Giaquinto et al. | |
| 5,907,406 A * | 5/1999 | Papaioannou et al. | 356/432 |
| 5,938,613 A * | 8/1999 | Shmulewitz | 600/461 |
| 5,999,836 A * | 12/1999 | Nelson et al. | 600/407 |
| 6,146,377 A * | 11/2000 | Lee et al. | 606/13 |
| 6,195,580 B1 | 2/2001 | Grable | |
| 6,243,484 B1 * | 6/2001 | Godik | 382/128 |
| 6,345,194 B1 * | 2/2002 | Nelson et al. | 600/425 |
| 6,480,281 B1 * | 11/2002 | Van Der Mark et al. | 356/432 |
| 6,675,037 B1 * | 1/2004 | Tsekos | 600/417 |
| 6,860,855 B2 * | 3/2005 | Shelby et al. | 600/459 |
| 6,883,194 B2 | 4/2005 | Corbeil et al. | |
| 7,171,256 B1 * | 1/2007 | Graessle et al. | 600/427 |
| 2002/0061090 A1 | 5/2002 | Lindstrom et al. | |
| 2006/0293597 A1 * | 12/2006 | Johnson et al. | 600/437 |

FOREIGN PATENT DOCUMENTS

| | | |
|---|---|---|
| EP | 845242 A2 | 3/1998 |
| FR | 2 653 005 | 4/1991 |
| GB | 2 277 664 A | 6/1993 |
| WO | WO 98/55013 | 12/1998 |
| WO | WO 01/35829 A1 | 5/2001 |

* cited by examiner

METHOD AND APPARATUS FOR OPTICAL IMAGING

CROSS-REFERENCE TO RELATED APPLICATIONS

This application is cross-referenced with U.S. patent application entitled "Method and Apparatus for Positioning a patient on a table for a Medical Procedure on a Breast" filed simultaneously herewith.

FIELD OF THE INVENTION

The invention relates to optical imaging. More specifically, it relates to optical imaging involving the use of a receptacle for holding an optical matching fluid having optical characteristics similar to breast tissue to facilitate breast imaging.

BACKGROUND OF THE INVENTION

Optical imaging is a new technique in the field of breast imaging. There are several attempts at replacing or complementing the standard x-ray technique used by most mammography apparatus in use today in clinics and hospitals. The standard mammography requires intense compression of the breast which is at best uncomfortable and at worst painful for the patient. Furthermore, x-rays may be harmful to the patient as ionizing radiation is introduced into the body.

Depending on the optical technology used, it may be necessary to conduct the probing energy between the different mediums through which the optical signal must travel. This is also the case when using ultrasound technology. It is known from U.S. Pat. No. 4,341,222 to have a flexible bag containing a fluid transmission medium. It is also known from U.S. Pat. No. 3,973,126 to immerse the breast in a fluid-filled chamber for an x-ray scanning technique. There is a need to adapt the method used for conducting probing energy to optical technology.

The article entitled "Developments Toward Diagnostic Breast Cancer Imaging Using Near-infrared Optical Measurements and Fluorescent Contrast Agents" by Hawrysz and Sevick-Muraca published in *Neoplasia*, Vol 2, No. 5, September-October, 2000, pages 388-417, provides a review of the use of near-infrared light for medical imaging, including breast imaging. As the technology for the imaging is developed and perfected, the mechanical aspects of the imaging must also be resolved and the apparatus used for the imaging must be constructed.

Furthermore, it is known from U.S. Pat. No. 6,195,580 to use lasers to obtain an image of a breast. However, the scanning system used is complex and the volume of breast tissue is not maximized by the techniques taught.

SUMMARY OF THE INVENTION

Accordingly, an object of the present invention is to provide an improved optical breast imaging apparatus.

Another object of the invention is to provide an improved receptacle for receiving a fluid used for optical breast imaging.

According to a first broad aspect of the present invention, there is provided an apparatus for optical imaging of a breast, the apparatus comprising: a supporting platform for positioning a patient in a face down prone position, the platform having a cavity for the breast to be pendantly suspended therethrough; a flexible fluid-filled receptacle below the cavity holding an optical matching fluid for the optical imaging, wherein the breast is immersed in the fluid during the optical imaging; a supporting mechanism surrounding a perimeter of the receptacle for supporting the receptacle within the cavity and preventing it from falling through the cavity when holding the optical matching fluid; and a source and detector coupling device for orienting source and detector ports with respect to the receptacle and for contacting the receptacle to obtain a desired geometry of the breast and the optical matching fluid.

Preferably, a valve is present on the bottom of the receptacle to empty and fill the receptacle with the optical matching fluid. A rim is provided around the opening of the receptacle as the supporting means. The rim is rigid and engages into a recess provided around the cavity in the supporting platform. Additionally, sealing flaps are provided above and below the rim to seal the optical matching fluid within the receptacle and avoid spilling.

Also preferably, the source and detector coupling means are a pair of parallel and substantially flat stabilizing plates that are also used to stabilize the breast and prevent any motion during imaging. The plates may move up, down, and rotate about a vertical axis.

According to a second broad aspect of the present invention, there is provided a method for supporting a breast for optical imaging, the method comprising: providing a supporting platform to position a patient in a face down position, the platform having a cavity for the breast to be pendantly suspended therethrough; suspending a flexible fluid-filled receptacle through the cavity to hold an optical matching fluid for the optical imaging; positioning the patient on the platform and immersing the breast in the optical matching fluid; orienting source and detector ports with respect to the receptacle and contacting the receptacle to obtain a desired geometry of the breast and optical matching fluid for the optical imaging.

Preferably, orienting the source and detector ports with respect to the receptacle is done by providing a pair of substantially flat and parallel plates that compress the receptacle. Also preferably, the breast is also compressed so as to prevent any motion during the imaging procedure.

According to a third broad aspect of the invention, there is provided a receptacle for use in optical imaging of a breast wherein a patient is lying face down on a supporting platform having a cavity for said breast to be suspended therethrough, and the receptacle is filled with an optical matching fluid for immersing, the receptacle comprising: a membrane defining an enclosed space with a substantially pear-shaped opening having a larger portion for receiving the breast and a narrower portion for receiving an axilla region adjacent to the breast.

According to a fourth broad aspect of the present invention, there is provided a receptacle for use in optical imaging of a breast wherein a patient is lying face down on a supporting platform having a cavity for said breast to be suspended therethrough, and the receptacle is filled with an optical matching fluid for immersing, the receptacle comprising: a membrane defining an enclosed space with an opening; and a first flared sealing flap projecting upwards from said opening around a perimeter such that said flap is flattened between said patient and said supporting platform in order to seal said optical matching fluid in said receptacle.

Preferably, a second supple sealing flap is also provided, the second flap projecting downwards from the opening around the perimeter such that the flap is flattened between the breast and an inner wall of the receptacle in order to seal the optical matching fluid in the receptacle.

BRIEF DESCRIPTION OF THE DRAWINGS

These and other features, aspects and advantages of the present invention will become better understood with regard to the following description and accompanying drawings wherein.

DETAILED DESCRIPTION OF THE PREFERRED EMBODIMENT

Figure 1:
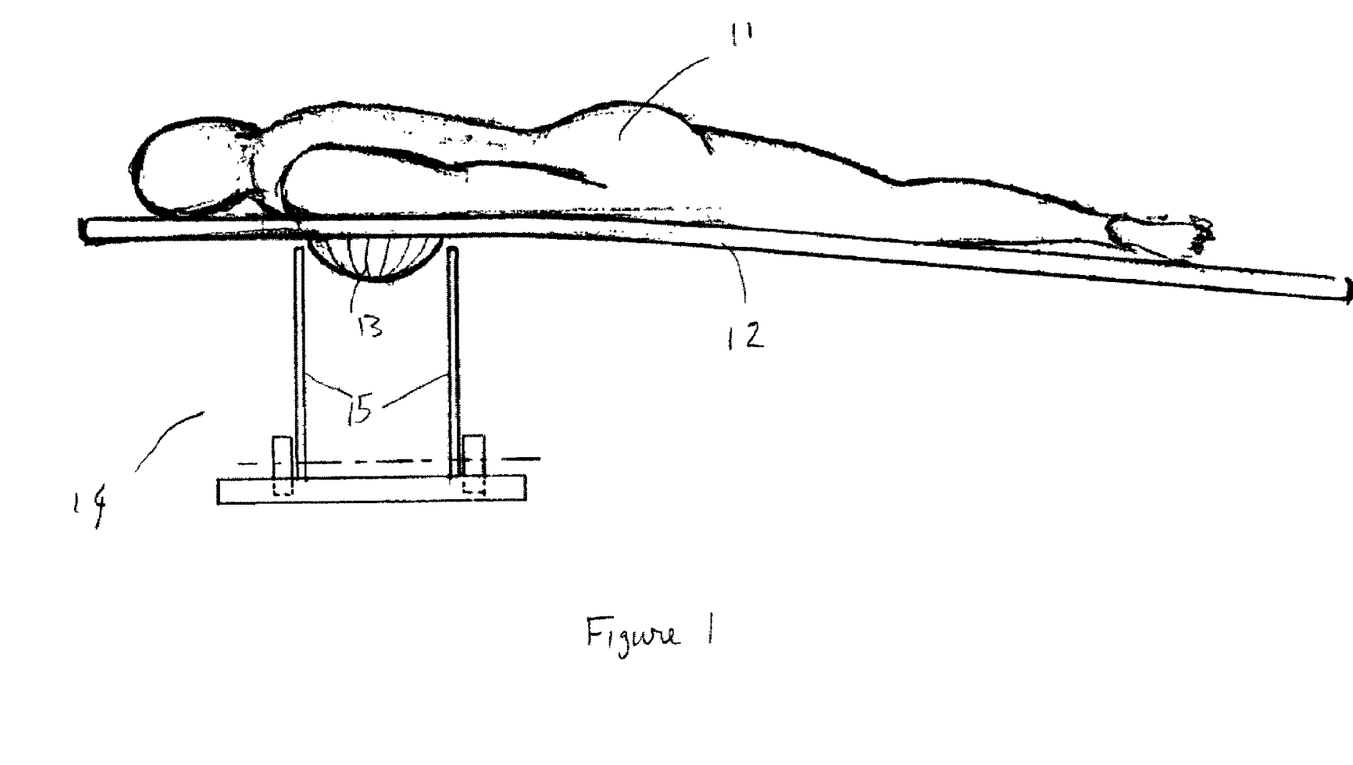
FIG. 1 is a diagram illustrating an apparatus according to the present invention.

FIG. 1 is a diagram representing a patient 11 lying face down on a supporting platform 12 for optical imaging of a woman's breast. A cavity is provided on the table to allow the breast to be pendantly suspended therethrough. A flexible, bag-like, fluid-filled receptacle 13 is suspended within the cavity. In the receptacle, an optical matching fluid typically having optical properties similar to milk is provided and the breast is immersed in the fluid during the optical imaging. Provided beneath the table at the level of the receptacle is a source and detector coupling device 14 for orienting source and detector ports with respect to the receptacle and for contacting the receptacle to obtain a desired geometry of the breast and the optical matching fluid.

The role of the coupling device is to modify the shape of the breast into a geometry that is simpler in order to be able to obtain images through complex reconstruction algorithms. Geometrical shapes that are currently known to be simple enough for the inverse solution software are parallelepipeds and cylinders. In the case of the parallelepipeds, the geometry is provided using a pair of parallel plates. The plates 15 are flat and vertical, as shown in FIG. 1.

The plates 15 are provided beneath the table and adjacent to the cavity. The plates are provided such that the breast can be scanned or imaged in all directions between −90° and +90°. Additionally, the range can be extended to +115° to −115°. The orientation of the plates is selected in order to reproduce X-Ray mammography standard views. It may or may not be necessary to contact the bag enough such that the breast is compressed. The additional compression is used to stabilize the breast and prevent any motion during imaging. The typical views taken of the breast are at 0° (the plates move along the axes of the table), 90° (the plates move perpendicular to the axes of the table), and 45° (the plates move diagonally). The plates, which are seen as two compression members in FIG. 1, form a rectangular cavity and can accommodate breasts of varying sizes. The two members move inwards for compression, as well as up and down with respect to the table, and also rotate about a substantially vertical axis.

Figure 2:
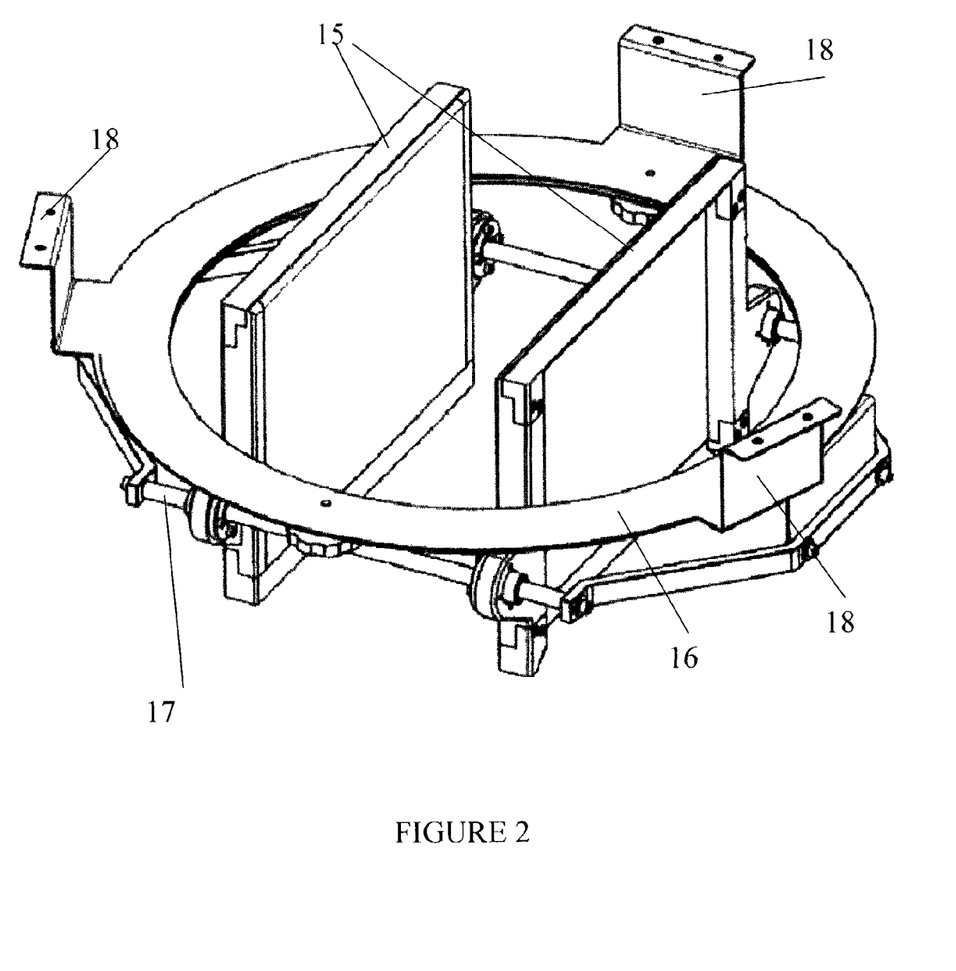
FIG. 2 is a diagram of the stabilizing plates assembly.

FIG. 2 is a schematic of the source and detector coupling device 14 shown in FIG. 1. In the preferred embodiment, plates 15 and a supporting frame provide the various degrees of motion of the plates. A circular support ring assembly 16 is connected to a base assembly 17 which is connected to the plates 15. The support ring assembly 16 can be connected to the bottom surface of the supporting platform via connecting means 18 or another frame which will hold the imaging equipment. The plates 15 are substantially transparent such that the laser pulses can go through them. In a preferred embodiment, a source port is present on one plate while a detector port is present on the opposite plate (not shown in figure). Alternatively, the source and detector ports can be present on the same plate. The light reflected back through the breast would then be detected from a position near the point of light injection.

Figure 3:
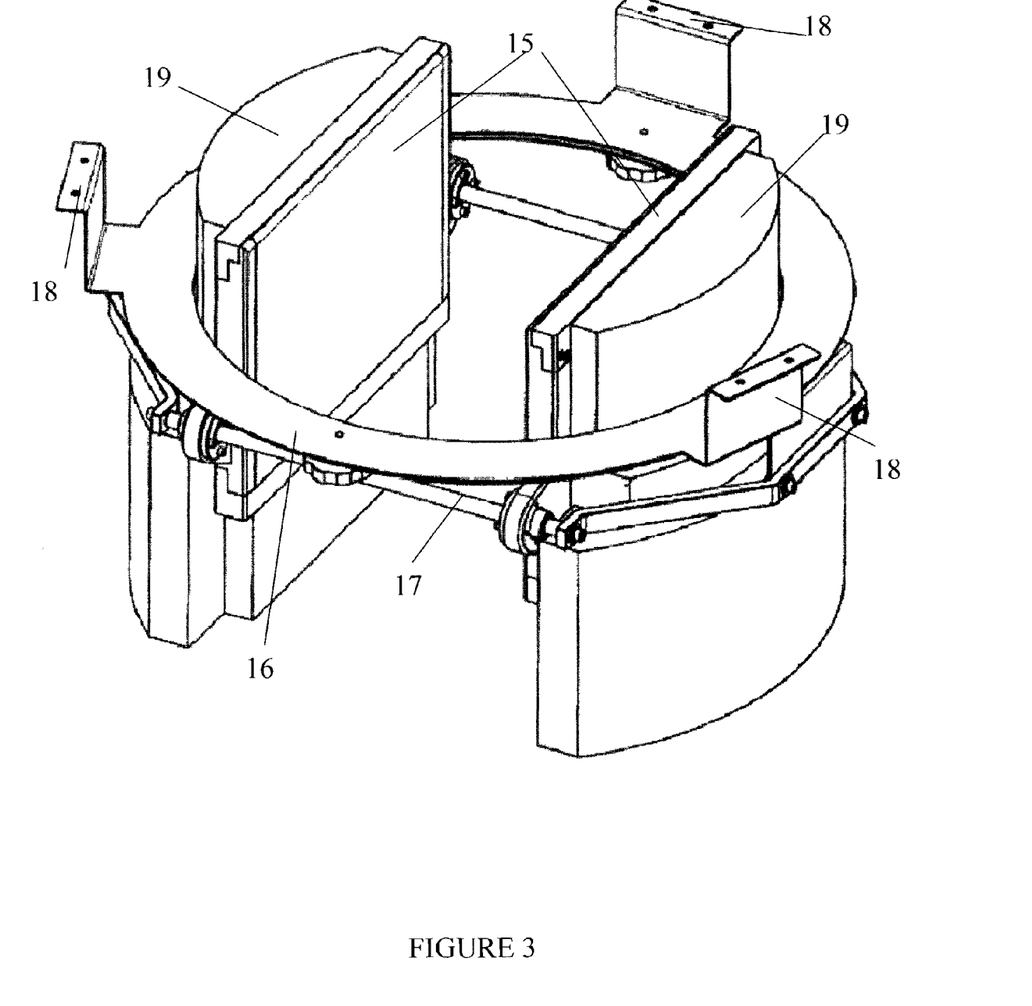
FIG. 3 is another diagram of the stabilizing plates assembly.

FIG. 3 is another schematic of the plate assembly. In this case, the plates are semi-circular and the optical imaging apparatus (source and detector) are provided within the area inside the back of the semi-circular elements 19. As can be seen from FIGS. 2 and 3, the plates are moved towards each other to compress the breast and away from each other to release the breast. The compression is very gentle, so as not to apply pressure to the breast but instead to stabilize it for the imaging procedure as well as possibly to improve geometry. The plates are also moved together upwards and downwards to access as much breast tissue as possible. This is achieved by having the top ends of the plates as near as possible to the rib cage of the patient. The mechanisms seen in FIGS. 2 and 3 also provide the rotating feature of the plates to reproduce the three standard x-ray views described above.

Alternatively, the plates do not need to be flat. The device can comprise a number of concave plates such that the concavity fits around the breast and cups it. This configuration is ideal to ensure stability of the breast. However, different ranges of breast size may require different radii of curvature for the plates. In this configuration, a cylindrical geometry may be obtained from the breast and optical matching fluid.

Another way of obtaining a cylindrical geometry of the breast and optical matching fluid is to have the source and detector coupling device in a circular configuration. The coupling device can be a single ring having a plurality of source and detector port positions. The ring would fit around the receptacle and compress it. As it would move along a vertical axis, a cylindrical shape would be formed by transmitting and detecting light at a plurality of steps along the vertical axis. The ring can start at the top or the bottom of the breast. Alternatively, an entire cylinder can comprise a plurality of source and detector ports and perform the imaging without having to move along the vertical axis. In this case, the imaging covers substantially 360° around the breast. In both the ring and cylinder case, the coupling device makes contact with the receptacle. The receptacle is filled with the optical matching fluid and a cylindrical geometry is obtained by having the contact. The device can also make contact with the breast in order to stabilize it and prevent motion during imaging.

Figure 4:
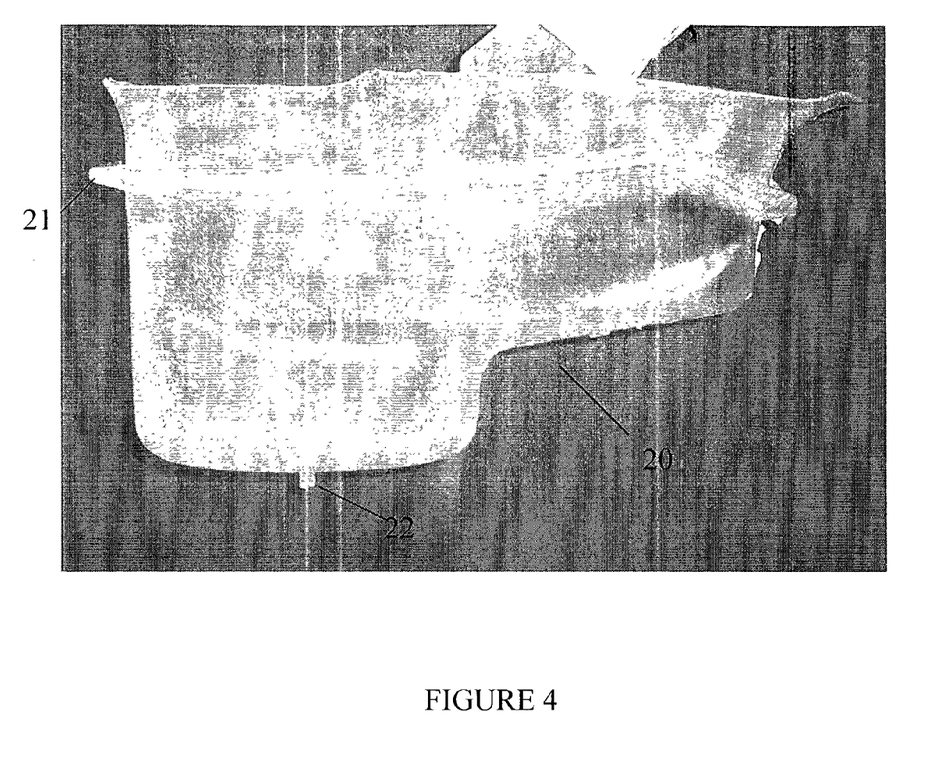
FIG. 4 is a side view of the receptacle for holding an optical matching fluid.

FIG. 4 is a side view of the receptacle 20 to be used to hold an optical matching fluid for the optical imaging. The receptacle 20 is placed within the cavity on the supporting platform and suspended therethrough. The receptacle 20 comprises a membrane defining an enclosed space having an opening. A supporting flange mechanism 21 is provided along the perimeter of the receptacle. In a preferred embodiment, the supporting mechanism 21 is a rim around the perimeter of the elastomeric receptacle that projects outwards. A thin, rigid, hollow member is inserted into a fold of the receptacle to create a rim. When the receptacle is inserted into the cavity, it engages into a recess provided for the rim so that the receptacle is securely supported and the weight of the fluid inside will not make it collapse through the cavity. It can be appreciated that a various number of methods may be used to support the receptacle holding the fluid within the cavity, such as water-proof tape, an elastic band around the perimeter of the opening, or any clamping mechanism used to hold the bag in place.

In a preferred embodiment, the receptacle is an elastomeric bag. Therefore, the rim can be made in one piece and inserted into the fold of the bag by stretching the material of the bag over the rim. Alternatively, the bag may not be elastomeric. In this case, a clamp may be used to hold the edges of the bag around a rigid rim that is fit into a recess provided around the cavity on the supporting platform. Such a clamp could comprise a hollow, pear-shaped disc placed on top of the bag on the supporting platform. The edges of the bag would then be contained between the top surface of the supporting platform and an additional rigid surface placed on top. The supporting platform may have a recess in the shape of the disc and surrounding the cavity deep enough that when the disc is in place and holds the bag, the top surface of the disc and the top surface of the platform are at the same level, thereby ensuring patient comfort.

The opening of the receptacle in one embodiment is elongated in shape such that the breast and adjacent axilla region can be immersed into the optical matching liquid. A valve 22 can be seen from the figure. This valve 22 is used to fill and empty the receptacle. A tube or conduit is connected from the valve 22 to a container for the optical matching fluid. An automated pumping system which can pump in and pump out the fluid may be provided. Alternatively, the container may be a bag, such as those used for intravenous (IV) purposes, and the fluid caused to flow towards the receptacle when the IV bag is lowered and away from the receptacle when the IV bag is raised.

Figure 5:
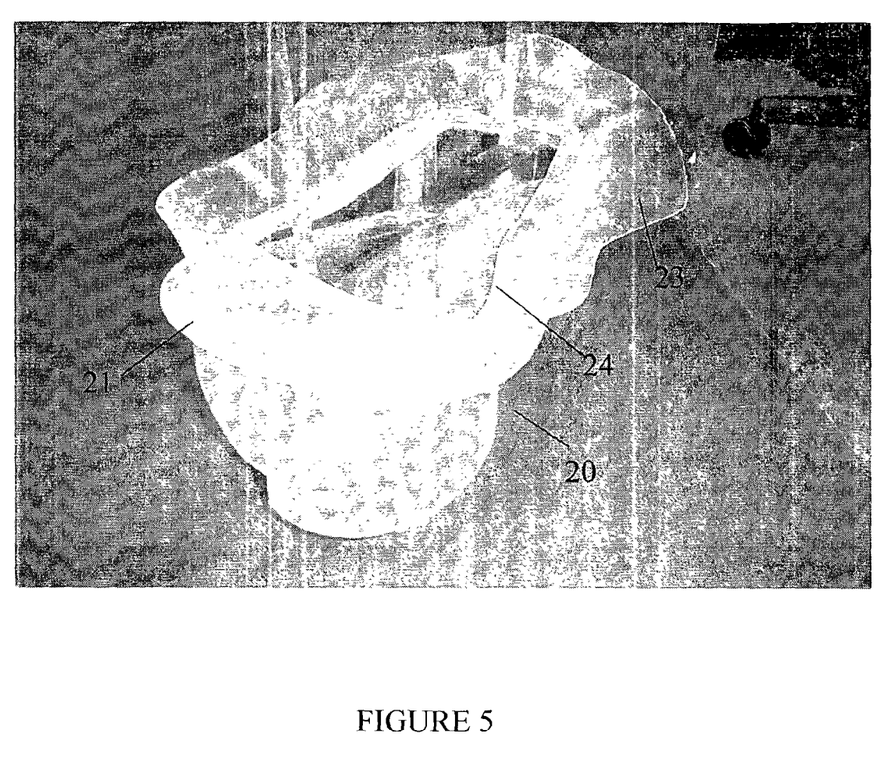
FIG. 5 is top perspective view of the receptacle of FIG. 4.

FIG. 5 is a top perspective view of the receptacle 20. The opening of the receptacle 20 is substantially pear-shaped such that the larger portion is for the breast and the narrower portion is for the adjacent axilla region. Sealing flaps 23 and 24 are provided to seal the liquid inside of the receptacle and prevent spilling onto the supporting platform. A first flared sealing flap 23 projects upwards from the opening and is located above the supporting mechanism. When the receptacle is in the cavity and the patient lies down on the supporting platform, the flap 23 is flattened downwards between the patient's body and the supporting platform. A second supple sealing flap 24 projects downwards from the opening and is located below the supporting means. The second sealing flap 24 is flattened between the patient's breast and the inner surface of the receptacle.

Figure 6:
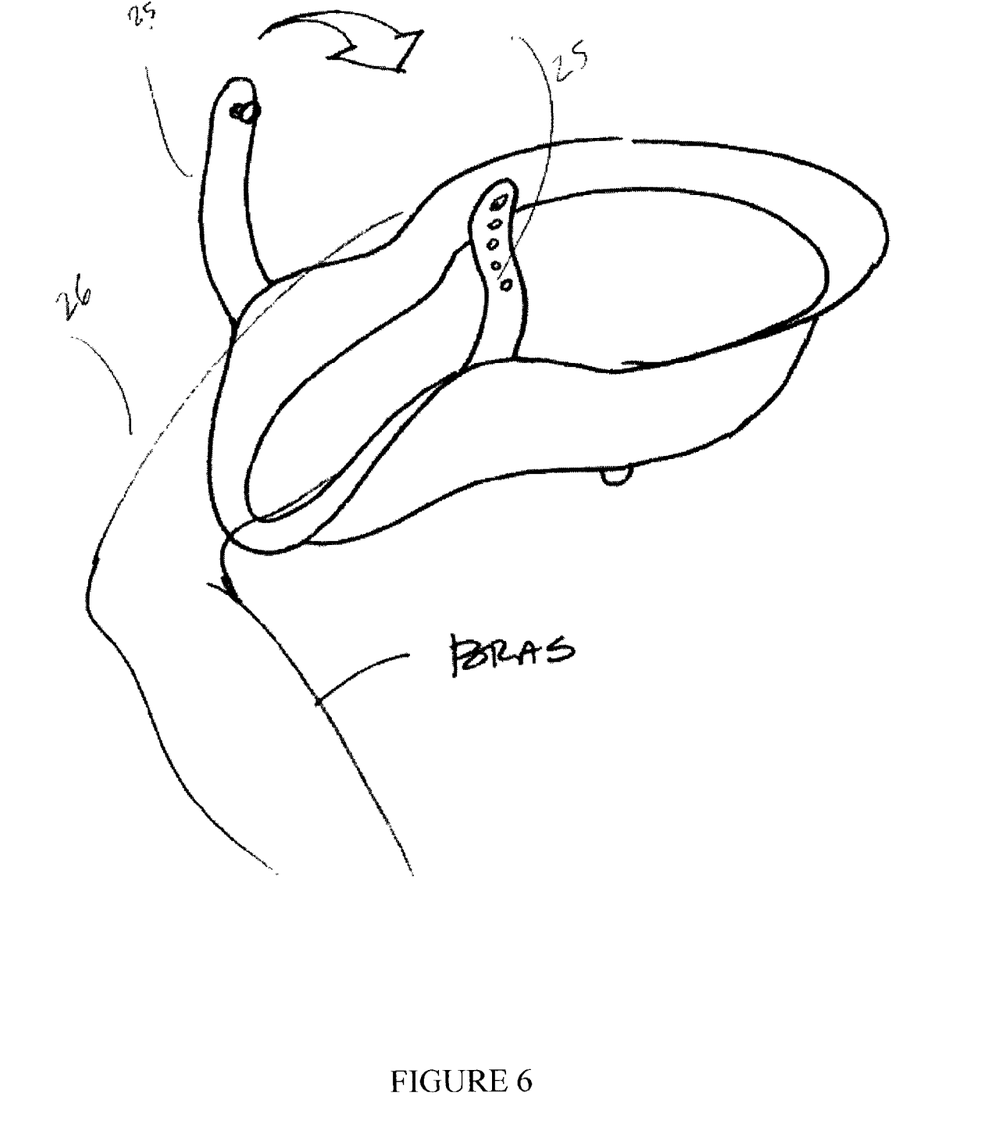
FIG. 6 is another diagram of the receptacle of FIG. 4.

FIG. 6 is a receptacle as described above with an additional feature for sealing the optical matching fluid within. A pair of attachments 25 are provided on each side of the receptacle to secure the receptacle around the arm 26 adjacent to the breast immersed in the optical matching fluid. Various fastening means can be used to secure the two attachments together, such as snaps, Velcro™ (hook and loop type fasteners), buttons, etc.

Additionally to the receptacle with the pear-shaped opening, a conical receptacle having a circular opening may be used. The bag-like receptacle is hemispherical and is used for optical imaging with the plates when the plates are placed at 0° and at 90°. In these cases, it is not necessary to have the extra space for the axilla region. The hemispherical receptacle allows the plates to be closer together, which contributes to producing a better image since the source and detector are closer to each other, and facilitates the formation of the desired geometry.

In a preferred embodiment, the material used for receptacle 20 is Silastic® 7-6830 Liquid Silicone Rubber (LSR) from Dow Corning in Midland, Mich. The LSR is a two-part silicone elastomer specifically designed for liquid injection molding or supported extrusion, dispersion coatings and films. When the A and B components are mixed together in equal portions, the liquid will cure to a tough, rubbery elastomer via addition cure (platinum cure) chemistry. The composition of the LSR is described in U.S. Pat. Nos. 4,753,978, and 5,036,117. A process of producing shaped. articles from liquid silicone rubber is described in U.S. Pat. No. 5,036,117. The properties of this product are similar to gum-based silicone rubber. Alternatively, other materials having equivalent flexible, translucent, elastomeric, and durable properties may be used and give an equivalent efficiency. Also possible is to use a simple bag made of a standard film or PVC material.

Figure 7:
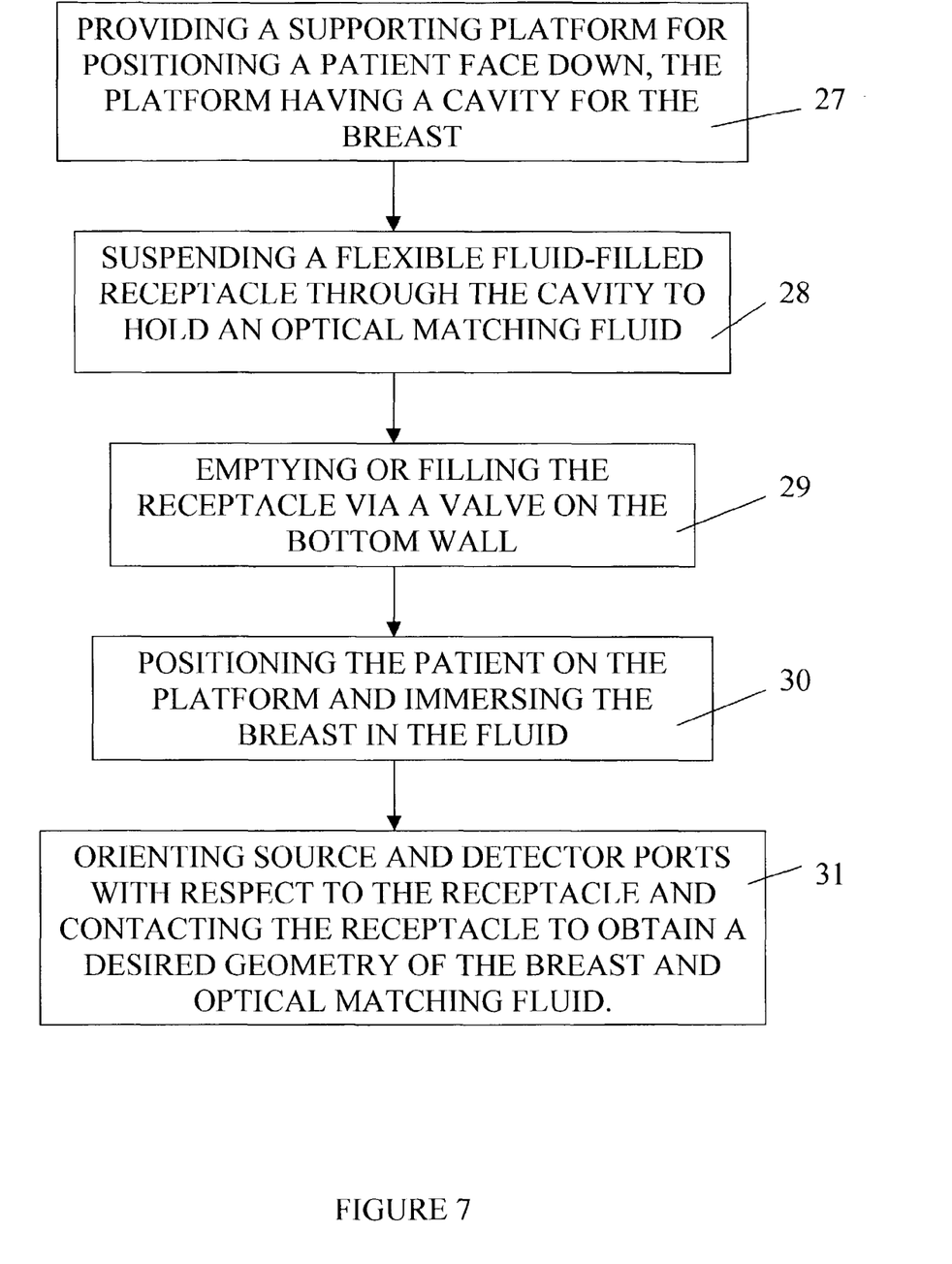
FIG. 7 is a flowchart of the method according to the present invention.

FIG. 7 is a flowchart of the method according to the present invention. The first step is to provide a supporting platform for positioning a patient face down in a prone position 27. The platform must have a cavity for the breast to be suspended therethrough, such as that seen in FIG. 1. A flexible receptacle is suspended through the cavity of the supporting platform 28. The receptacle holds an optical matching fluid for the optical imaging. In order to suspend the receptacle, supporting means are provided around a perimeter of the receptacle. A preferred embodiment for the supporting means is a solid rim that engages into a recess provided around the cavity of the supporting platform.

The receptacle is filled and emptied via a valve provided on the bottom wall of the receptacle 29. A tube is connected between the valve and means for filling and emptying the receptacle. One embodiment of the means is a bag holding the liquid, wherein raising and lowering the bag causing the liquid to exit and enter the receptacle through the valve, respectively. Another embodiment is an automatic pumping mechanism that will pump in the liquid and retrieve the liquid by reversing the pumping process. The fluid is kept warm and regulated for patient comfort.

The patient is then positioned on the supporting platform and the breast is immersed into the fluid in the receptacle 30. A pair of source and detector ports are positioned on a source and detector coupling device. The device is oriented with respect to the receptacle and the receptacle is contacted in order to obtain a desired geometry of the breast and the optical matching fluid 31. Of course, it is possible to immerse the breast first and then fill the receptacle using the filling mechanisms described above.

In a preferred embodiment, the breast is stabilized with a pair of parallel stabilizing plates by pressing gently against the flexible receptacle until the plates can hold the breast in place. The breast is then imaged by transmitting and detecting an optical pulse sent through the breast. Preferably, the imaging is done from three different perspectives comprising a horizontal (plates positioned parallel to length of body), vertical (plates positioned perpendicular to length of body), and diagonal (plates positioned diagonally to length of body) compression of the stabilizing plates.

Additionally, when immersing the breast, the optical matching fluid may be sealed into the receptacle by providing a first sealing flap projecting upwards from the perimeter and located above the rim such that the flap is flattened between the patient's body and the supporting platform. A second sealing flap projecting downwards from the perimeter and located below the rim can also be provided such that the flap is flattened between the breast and an inner wall of the receptacle.

The optical matching fluid used is a fluid that is chosen to match the optical of the breast tissue, such as Intralipid 90™. Alternatively, other fluids with similar properties can be used.

The fluid is also used to maintain geometry when imaging the breast. The geometry is important because the source scans the stabilizing plate in a raster scan and covers a surface area of a substantially rectangular shape. If the detector is placed exactly opposite the source and follows its motion in the raster scan, there is a possibility that the source will send a pulse in an area where there is no breast tissue. If this were to happen and the breast was not immersed in a liquid, the laser pulse would not be attenuated by any medium (breast tissue, liquid), and the detector would receive a pulse of extremely high intensity and could damage the detecting device. Additionally, the mathematical algorithms used to do imaging can be solved only for specific geometries, such as parallelepipeds and cylinders. The optical matching fluid is used to obtain the desired geometry by matching it with the breast and molding the receptacle holding the liquid into the desired geometry.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. An apparatus for optical imaging of an object, the apparatus comprising:
    a pair of substantially flat, light transmitting plates mounted to be essentially vertical and parallel to one another;
    a flexible optical matching fluid reservoir adapted to be filled with optical matching fluid and adapted to immerse therein said object;
    a positioning mechanism for circumferentially adjusting position of said plates about said object and adjusting a relative spacing between said plates while remaining essentially vertical and parallel to one another, said plates being adapted to apply pressure to said object while the object is located in the reservoir and immersed in said matching fluid so as to form essentially a parallelepiped with said optical matching fluid and the object to obtain a desired geometry of said object and said optical matching fluid;
    a source and detector arranged outside said plates for emitting light into and receiving light from said object immersed in the reservoir and surrounded by said optical matching fluid; and
    a supporting mechanism comprising a rigid rim and a supporting platform, the supporting mechanism surrounding an upper perimeter of said reservoir, said supporting platform comprising an area surrounding said cavity for receiving said rigid rim, said rigid rim being formed in one piece and being inserted into a fold around said upper perimeter.

2. An apparatus as claimed in claim 1, wherein said source and detector comprise ports on opposite plates.

3. An apparatus as claimed in claim 1, wherein said plates can move upwards, downwards, and rotate about a substantially vertical axis with respect to the supporting mechanism.

4. An apparatus as claimed in claim 1 wherein said reservoir comprises a valve in a bottom wall for filling and emptying of said optical matching fluid.

5. An apparatus as claimed in claim 1, wherein said reservoir comprises a flexible, fluid-filled receptacle that is elongated in shape such that an axilla region adjacent to said breast is also submerged in said optical matching fluid.

6. An apparatus as claimed in claim 5, wherein said shape is a pear-shape such that said axilla region resides in a narrower portion of said receptacle and said breast resides in a larger portion of said receptacle.

7. An apparatus for optical imaging of an object, the apparatus comprising:
    a pair of substantially flat, light transmitting plates mounted to be essentially vertical and parallel to one another;
    a flexible optical matching fluid reservoir adapted to be filled with optical matching fluid and adapted to immerse therein said object;
    a positioning mechanism for circumferentially adjusting position of said plates about said object and adjusting a relative spacing between said plates while remaining essentially vertical and parallel to one another, said plates being adapted to apply pressure to said object while the object is located in the reservoir and immersed in said matching fluid so as to form essentially a parallelepiped with said optical matching fluid and the object to obtain a desired geometry of said object and said optical matching fluid;
    a source and detector arranged outside said plates for emitting light into and receiving light from said object immersed in the reservoir and surrounded by said optical matching fluid; and
    a supporting mechanism surrounding an upper perimeter of said reservoir wherein said plates and said reservoir are independent, and said reservoir is made of an elastomeric silicone.

8. An apparatus as claimed in claim 7, wherein said reservoir comprises a flexible fluid-filled receptacle with a first flared sealing flap projecting upwards from said perimeter and located above said patient supporting platform such that said flap is flattened between said patient and said supporting platform in order to seal said optical matching fluid in said receptacle.

9. An apparatus as claimed in claim 8, wherein said flexible fluid-filled receptacle comprises a second supple sealing flap projecting downwards from said perimeter and located below said patient supporting platform such that said flap is flattened between said breast and an inner wall of said receptacle in order to seal said optical matching fluid in said receptacle.

10. A method for supporting an object for optical imaging, the method comprising:
    providing a pair of substantially flat, light transmitting plates mounted to be essentially vertical and parallel to each other;
    providing a positioning mechanism for circumferentially adjusting position of said plates about said object;
    providing a flexible optical matching fluid reservoir and transferring into the reservoir an optical matching fluid for said optical imaging;
    locating said object within the reservoir by suspending a flexible receptacle filled with the optical matching fluid, and positioning said patient so as to locate a breast within the receptacle such that it is immersed in said fluid and positioned between the plates, wherein said suspending comprises providing a rigid rim around a perimeter of said receptacle and providing an area surrounding said cavity in said supporting platform for receiving said solid rim; and positioning said plates so as to apply pressure to said object while the object is immersed in said matching fluid in said reservoir so as to form a substantially parallelepiped geometry of said object and optical matching fluid.

11. A method as claimed in claim 10, further comprising providing source and detector ports on opposite ones of said plates.

12. A method as claimed in claim 10, further comprising at least one of filling and emptying said reservoir via a valve provided on a bottom wall of said reservoir.

13. A method as claimed in claim 10, wherein said immersing comprises immersing an axilla region adjacent to said breast into said optical matching fluid such that breast tissue from said axilla region is also imaged.

14. A method as claimed in claim 10, wherein said immersing comprises sealing said optical matching fluid into said receptacle by providing a first sealing flap projecting upwards from said perimeter and located above said rim such that said flap is flattened between said patient and said supporting platform in order to seal said optical matching fluid in said receptacle.

15. A method as claimed in claim 14, wherein said sealing further comprises providing a second sealing flap projecting downwards from said perimeter and located below said rim such that said flap is flattened between said breast and an inner wall of said receptacle in order to seal said optical matching fluid in said receptacle.

* * * * *